(12) United States Patent
Steppe

(10) Patent No.: US 7,565,972 B2
(45) Date of Patent: Jul. 28, 2009

(54) MEDICAL EQUIPMENT TRAY SYSTEM

(75) Inventor: Dennis L. Steppe, Corona, CA (US)

(73) Assignee: Alcon, Inc., Hunenberg (CH)

( * ) Notice: Subject to any disclaimer, the term of this patent is extended or adjusted under 35 U.S.C. 154(b) by 142 days.

(21) Appl. No.: 11/820,151

(22) Filed: Jun. 18, 2007

(65) Prior Publication Data

US 2008/0308698 A1 Dec. 18, 2008

(51) Int. Cl.
*B65D 83/10* (2006.01)
(52) U.S. Cl. .................................. 206/370; 206/438
(58) Field of Classification Search ............... 206/363, 206/364, 367–370, 438; 220/23.9, 495.01; 248/309.1, 311.2, 323; 422/300, 302, 297, 422/299
See application file for complete search history.

(56) References Cited

U.S. PATENT DOCUMENTS

| | | | |
|---|---|---|---|
| 3,696,920 A | 10/1972 | Lahay | |
| 4,596,329 A * | 6/1986 | Eldridge, Jr. | 206/370 |
| 5,226,892 A | 7/1993 | Boswell | |
| 5,350,357 A | 9/1994 | Kamen et al. | |
| 5,433,929 A * | 7/1995 | Riihimaki et al. | 422/297 |
| 5,464,025 A | 11/1995 | Charles et al. | |
| 5,482,067 A * | 1/1996 | Wittrock et al. | 206/363 |
| 6,012,586 A * | 1/2000 | Misra | 206/571 |
| 6,099,812 A * | 8/2000 | Allen et al. | 422/300 |
| 6,217,835 B1 * | 4/2001 | Riley et al. | 422/297 |
| 6,632,189 B1 | 10/2003 | Fallen et al. | |
| 6,634,499 B2 * | 10/2003 | Allen et al. | 206/370 |
| 6,705,474 B1 | 3/2004 | Buczek | |
| 7,243,791 B2 * | 7/2007 | Detruit et al. | 206/363 |
| 2003/0055387 A1 | 3/2003 | Sutton et al. | |
| 2006/0086634 A1 | 4/2006 | Steppe | |

OTHER PUBLICATIONS

English language abstract for JP 2002200096, 2002, 1 pg.

* cited by examiner

*Primary Examiner*—Luan K Bui
(74) *Attorney, Agent, or Firm*—W. David Lee

(57) ABSTRACT

A medical equipment tray system includes a two piece platform, a foldable liner which fits over the two piece platform and a handpiece cradle which may be elevated with respect to the two piece platform.

11 Claims, 7 Drawing Sheets

MEDICAL EQUIPMENT TRAY SYSTEM

CROSS-REFERENCE TO RELATED APPLICATIONS

N/A

STATEMENT REGARDING FEDERALLY SPONSORED RESEARCH OR DEVELOPMENT

N/A

NAMES OF THE PARTIES TO A JOINT RESEARCH AGREEMENT

N/A

REFERENCE TO SEQUENCE LISTING

N/A

BACKGROUND OF THE INVENTION

1. Field of the Invention

The present invention pertains to instrument tray systems; more particularly, the present invention pertains to instrument tray systems associated with medical/surgical systems.

2. Description of the Related Art

A common accessory associated with medical/surgical systems, and more particularly ophthalmic surgical systems such as phacoemulsifiers and vitrectomy units, is a reusable tray system. These reusable instrument tray systems are typically made from either stainless steel or an autoclavable plastic. The instrument tray systems are designed to interface with an articulating arm and tray support attached to the surgical system. Many tray systems contain pockets or cavities sized and shaped to hold the various instruments, devices, handpieces and consumables used during a specific surgical procedure.

While many prior art tray systems are in use, problems still remain with such tray systems.

Some of the problems with commonly available instrument tray systems are:

a) the instrument tray system is too small to hold all of the needed instruments, devices, handpieces and consumables associated with a specific surgical procedure;

b) The instrument tray system is too large to fit into available autoclave sterilizers;

c) The hard surface of the instrument tray system can damage delicate instruments used in a surgical procedure.

Accordingly, a need remains in the art for an instrument tray system which solves the foregoing problems.

BRIEF SUMMARY OF THE INVENTION

The disclosed medical equipment tray system is large enough to hold a complete set of needed instruments, devices, handpieces and consumables; fits within an autoclave sterilizer; and will not damage delicate instruments. The disclosed tray system includes a foldable platform, a foldable liner, and an elevatable handpiece cradle.

BRIEF DESCRIPTION OF THE DRAWINGS

A better understanding of the medical equipment tray system of the present invention may be had by reference to the drawing figures wherein.

DETAILED DESCRIPTION OF THE INVENTION

Figure 1:
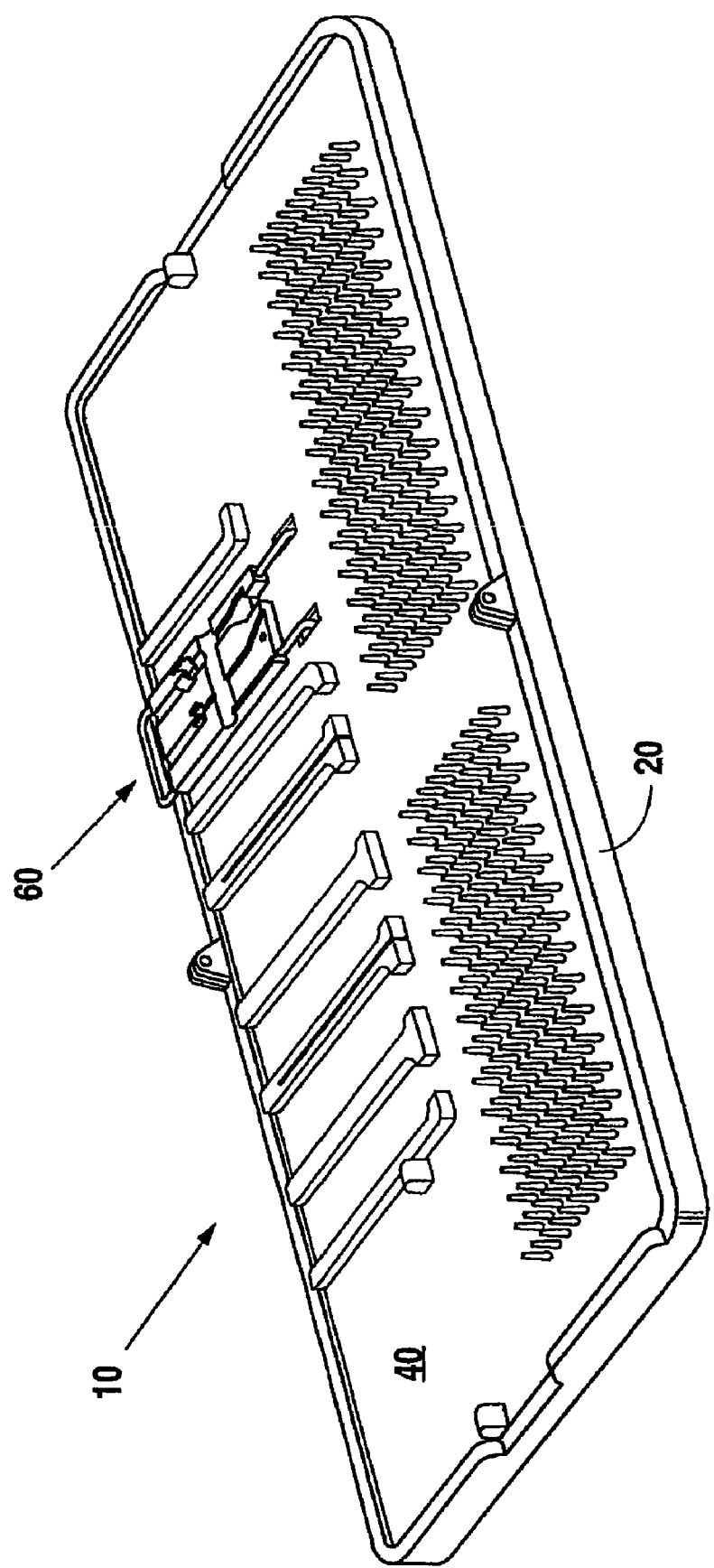
FIG. 1 is a perspective view of the disclosed medical equipment tray system.

The medical equipment tray system 10 of the preferred embodiment of the present invention as shown in FIG. 1 includes three parts: a platform portion 20, a foldable liner 40, and a handpiece cradle 60.

Figure 2:
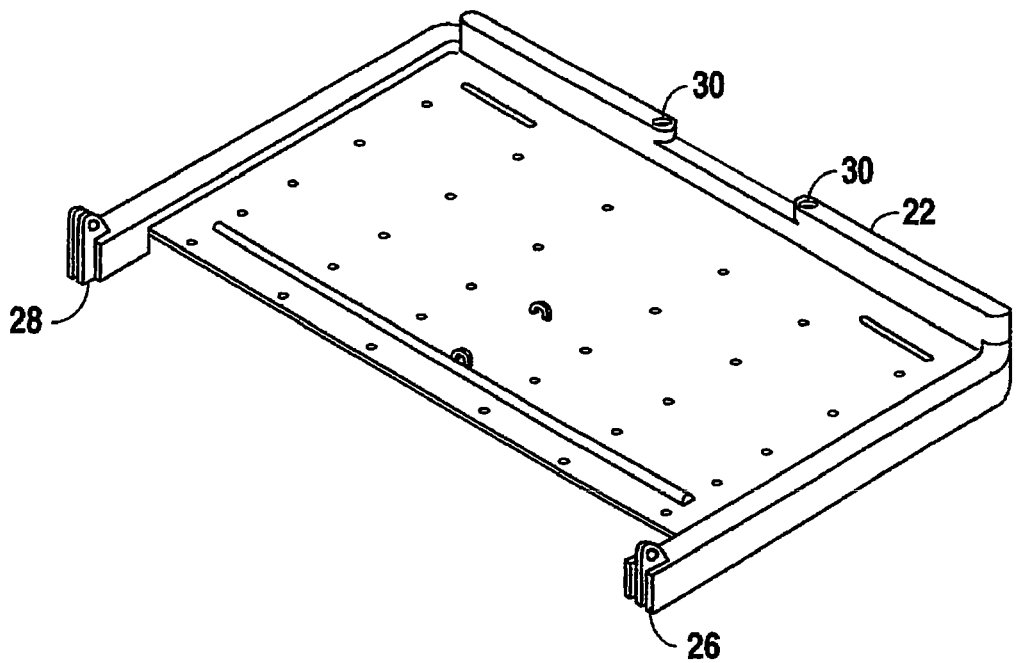
FIG. 2 is a perspective view of the first support section of the molded platform.
Figure 3:
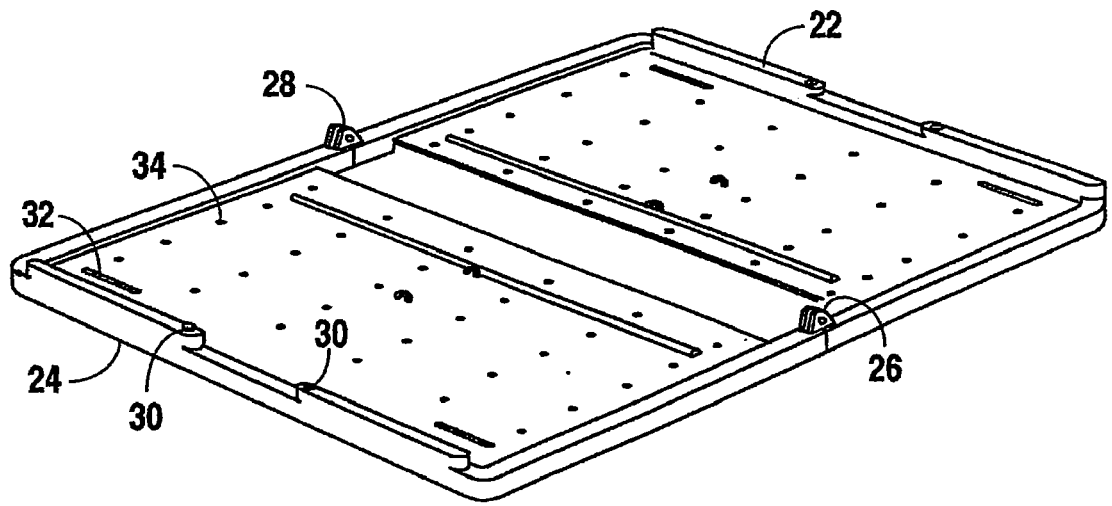
FIG. 3 is a perspective view of the first and second support sections of the molded platform.
Figure 4:
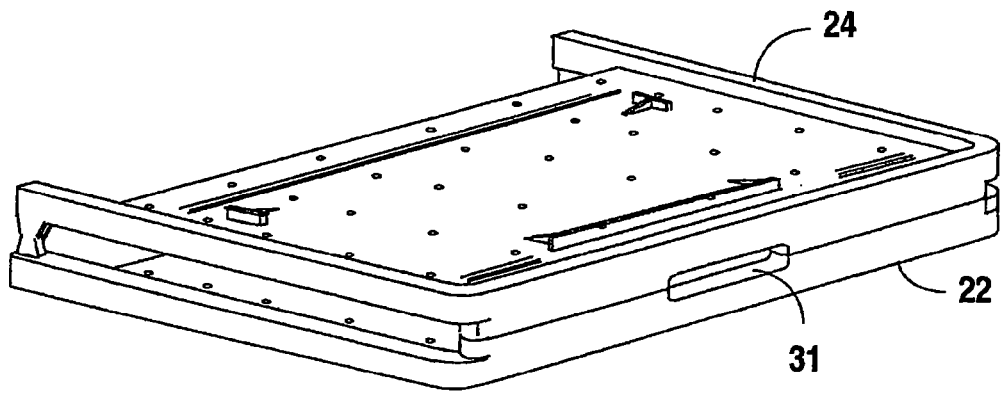
FIG. 4 is a perspective view of the first and second support sections folded together.

The platform portion 20 of the tray system 10 is preferably an injected molded part made out of an autoclavable plastic material. Two platform sections 22, 24 as shown in FIGS. 2 and 3 preferably form each tray system 10. Each section has a male and female hinge 26, 28 that join platform sections 22, 24 together as shown in FIG. 3. A lock on the male hinge 26 of one section interfaces with the female hinge 28 of the other section to keep the joined platform in an open position as shown in FIG. 3. By bringing the opposing sides of the platform sections together, the lock is overcome and the platform is allowed to fold so that section 24 rests on section 22, as shown in FIG. 4. Male and female button locks 30 are used to keep the folded platform in a closed position until the platform 20 is opened using the finger relief 31 formed by the two folded platform sections 22, 24.

Figure 5:
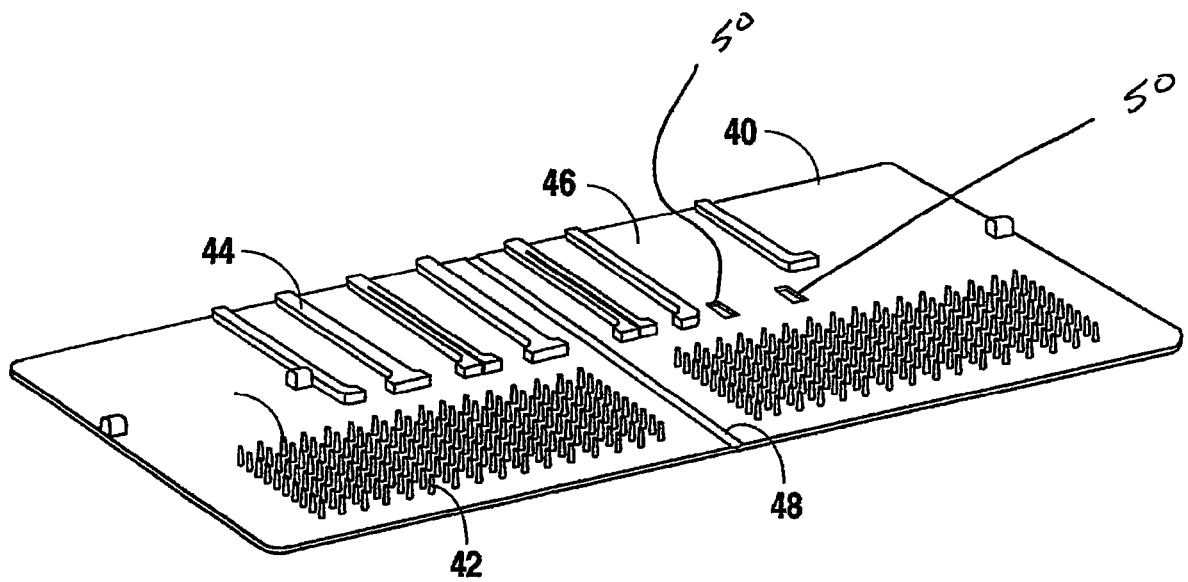
FIG. 5 is a perspective view of the liner which rests on the first and second support sections.
Figure 6:
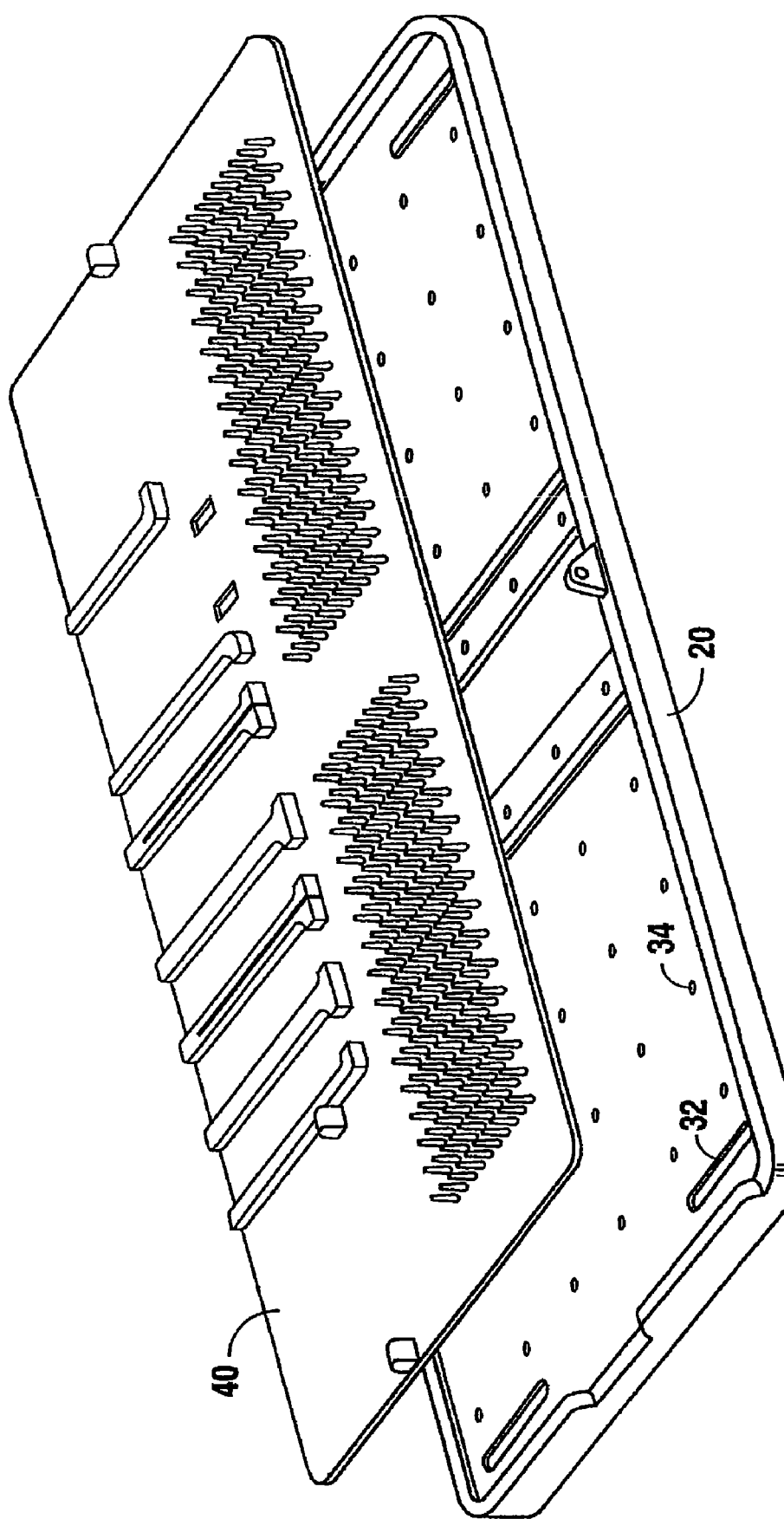
FIG. 6 is a perspective view of the position of the liner with respect to the first and second support sections.

The foldable liner 40 shown in FIG. 5 is preferably a molded component made out of silicon elastomer. Foldable liner 40 provides the surface that is used to position the instruments, devices, handpieces and consumables that may be used during a surgical procedure. Accordingly, the foldable liner 40 includes a plurality of projections 42, 44 extending upwardly therefrom. Projections 42, 44 have spaces therebetween that enable the organization and positioning of the instruments, devices, handpieces and consumables to be used. The soft upper surface 46 of the foldable liner 40 protects the various devices placed thereupon from damage. The foldable liner 40 press fits into openings such as linear cuts 32 and round holes 34 found in the platform 20 as shown in FIGS. 3 and 6. The foldable liner 40 is molded to be thinner along a centrally located hinge line 44-48 which is positioned over that portion of molded platform 20 where the two sections 22, 24 come together. This hinge line 44-48 allows the foldable liner 40 to fold more easily when the molded platform 20 is folded into its sterilization position as shown in FIG. 4.

Figure 7:
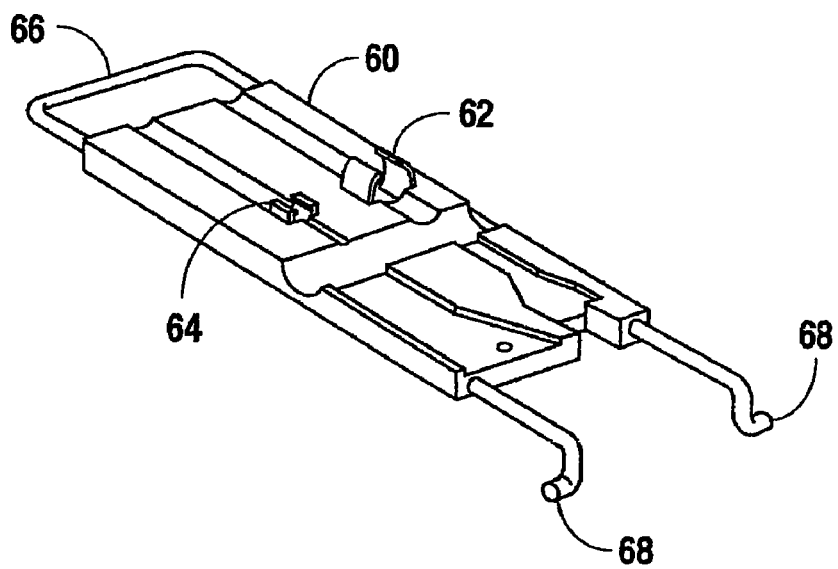
FIG. 7 is a perspective view of the handpiece cradle.
Figure 8:
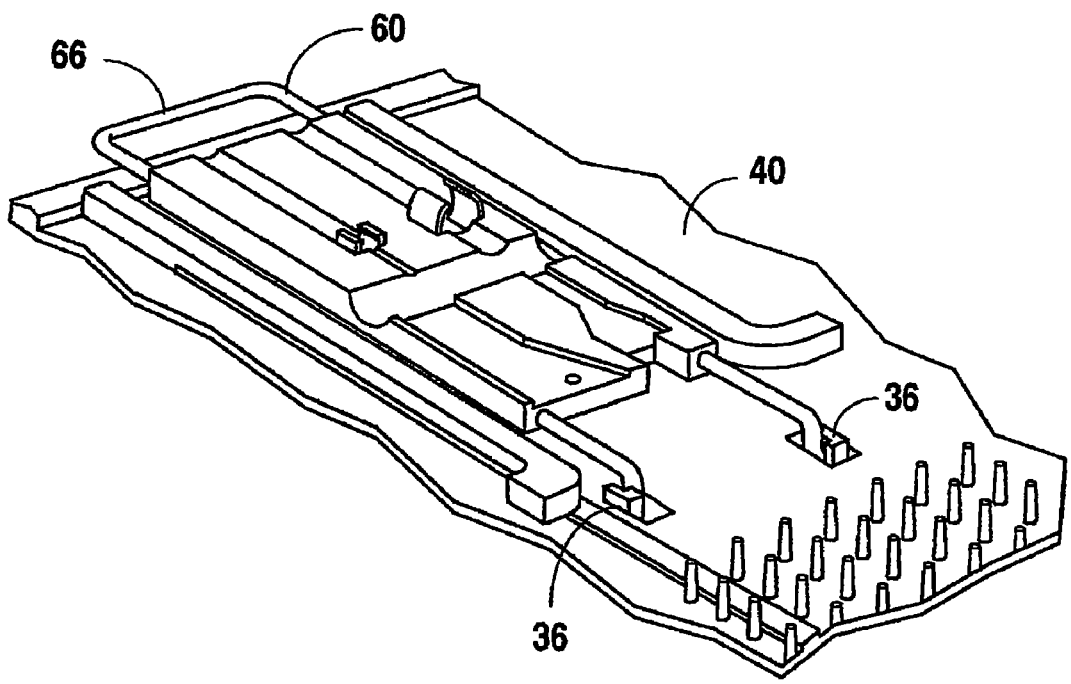
FIG. 8 is a perspective view of the hinged mounting of the handpiece cradle.
Figure 9:
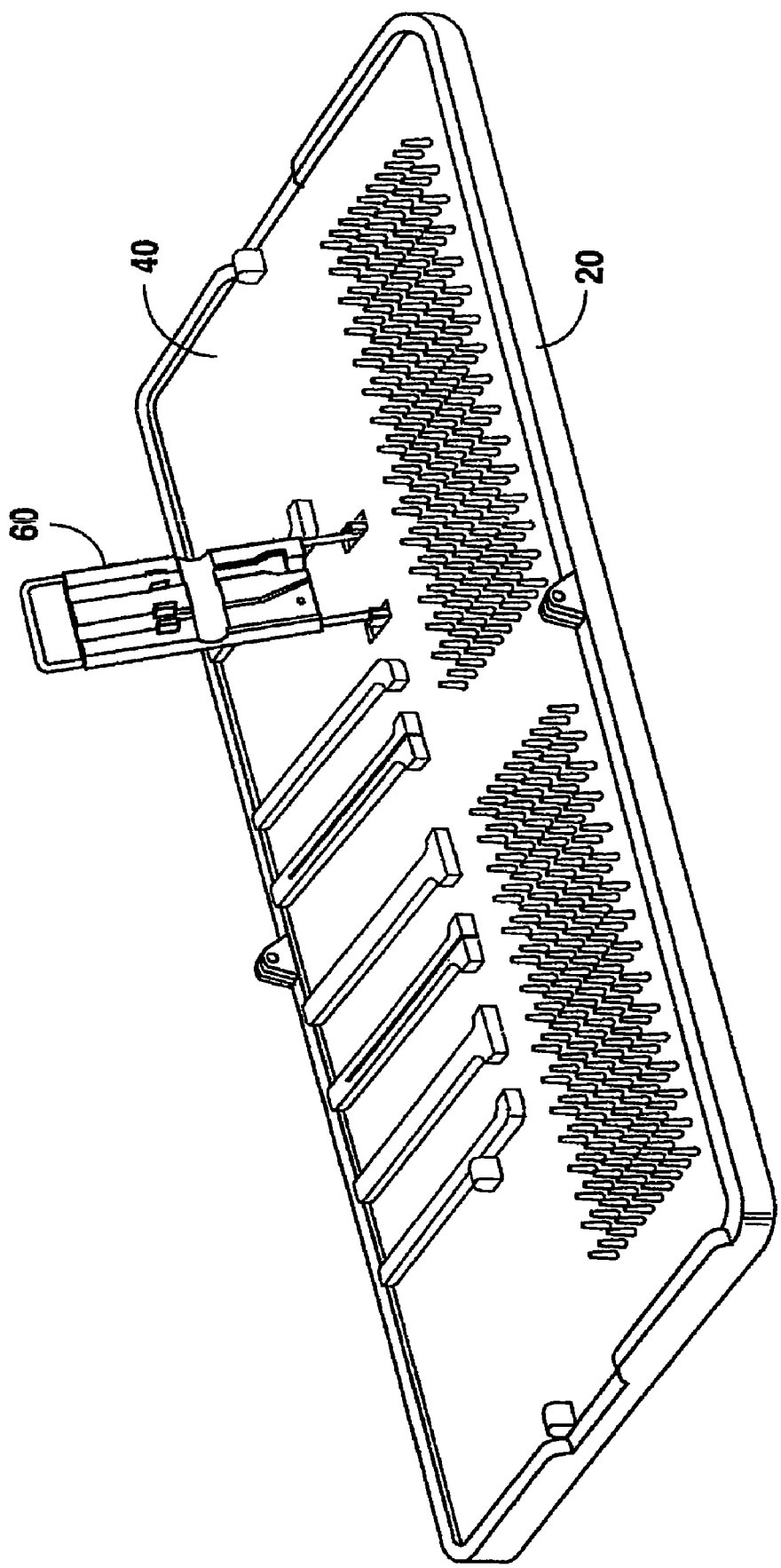
FIG. 9 is a perspective view of the handpiece cradle elevated from the tray system.
Figure 10:
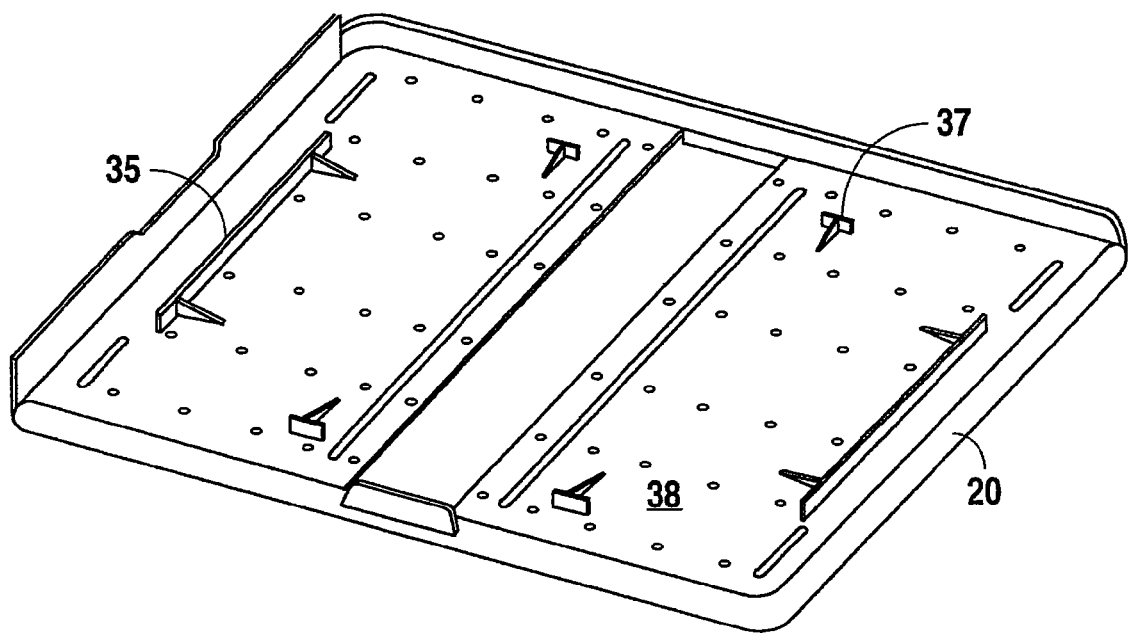
FIG. 10 is a perspective view of the bottom of the first and second support sections.

The handpiece cradle 60 is an injected molded part made out of an autoclavable plastic material as shown in FIGS. 7 and 8. The handpiece cradle 60 has spaces 62, 64 on which surgical handpieces, such as an ultrasonic handpiece or an irrigation/aspiration handpiece, may be placed. The handpiece cradle 60 has a handle 66 and male hinge portions 68. The male hinge portions 68 assemble into female hinge portions 36 on the platform 20 as shown in FIG. 8. These female hinge portions 36 protrude through cutouts 50 in the foldable liner 40. When the handpiece cradle 60 is assembled to the platform 20, it can be elevated to a vertical position via handle 66, as shown in FIG. 9. Locks on the female hinge portions 36 lock the elevatable handpiece cradle 60 in its vertical position as well as in its horizontal position, as shown in FIG. 1. The elevatable handpiece cradle 60 facilitates priming of the ultrasonic and/or irrigation/aspiration handpieces.

Figure 11:
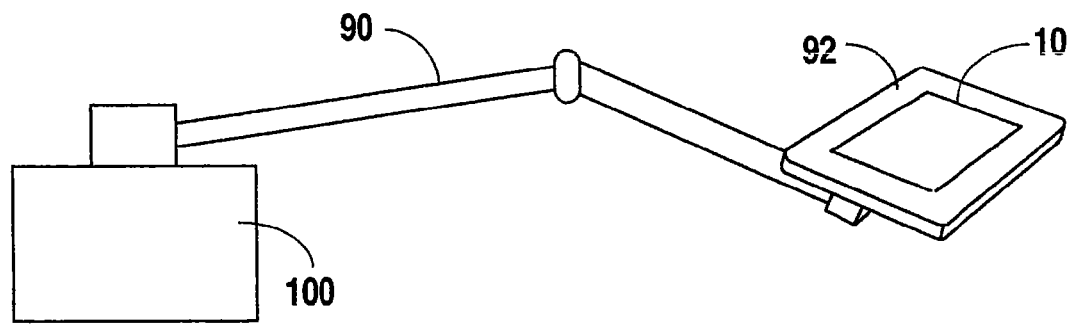
FIG. 11 is a schematic, perspective view of an articulating arm and support for the tray system.

In the unfolded position, the tray system 10 can be used as a procedural set-up tray that can be placed on support 92 such as a table or Mayo stand at the end of an articulating arm 90 of a medical/surgical system 100, as shown in FIG. 11. The tray system 10 is sized so that it can fit onto either a large or a small Mayo stand. Molded features 35 on the bottom 38 of the platform 20 locate and secure the tray system 10 to a large Mayo stand. Molded features 37 on the bottom 38 of the platform 20 locate and secure the tray system 10 to a small Mayo stand.

While the medical equipment tray system of the present invention has been described by reference to its preferred embodiment, those of ordinary skill in the art will understand that the foregoing disclosure embodies other embodiments. Such other embodiments shall be included within the scope and meaning of the appended claims.

What is claimed is:

1. A tray system for sterilization and set up of medical instruments, devices, handpieces or consumables to be used in a medical/surgical procedure, said tray system comprising:
   a first platform section and a second platform section, said first and second platform sections hingedly connected one to another to enable a first folded position wherein said first platform section is positioned over said second platform section and a second unfolded position wherein said first platform section and said second platform section form a substantially planar surface;
   a foldable liner having projections and spaces for organizing and positioning the instruments, devices, handpieces and consumables, said foldable liner constructed and arranged for attachment to said first and second platform sections in both said first folded position and said second unfolded position; and
   handpiece cradle hingedly connected to one of said first platform section and said second platform section and positioned over said foldable liner, said handpiece cradle movable to an unelevated postion proximate said foldable liner to enable said first folded position, and said handpiece cradle movable to an elevated postion in said second unfolded position to enable of and priming of a surgical handpiece.

2. The tray system as defined in claim 1 wherein said tray system is sized to enable sterilization in an autoclave in said first folded position.

3. The tray system as defined in claim 1 wherein said foldable liner has a soft upper surface.

4. The tray system as defined in claim 3 wherein said foldable liner is made from a silicon elastomer.

5. The tray system as defined in claim 1 wherein said foldable liner is attached to said first platform section and said second platform section using a press fit.

6. A system for positioning medical instruments, devices, handpieces or consumables near the user of a medical/surgical system, said system comprising:
   an articulating arm having a stationary end attached to the medical surgical system and a movable end which is positionable by the user of the medical/surgical system;
   a support for a tray located on said movable end of said articulating arm; and
   an equipment tray system constructed and arranged for mounting on said support, said equipment tray system including:
      a platform portion having two sections, said two sections being hingedly connected one to another and arranged for folding one platform section over the other platform section; and
      a liner having projections and spaces for organizing and positioning instruments, devices, handpieces, or consumables, said liner constructed and arranged for fitment over said platform portion; and
      a handpiece cradle hingedly connected to one of said platform sections and positioned over said liner, said handpiece cradle movable to an unelevated position proximate said liner, and said handpiece cradle movable to an elevated position to enable support of and priming of a surgical handpiece.

7. The system as defined in claim 6 wherein said equipment tray system is sized to enable sterilization in an autoclave when said platform sections are folded one over the other.

8. The system as defined in claim 6 wherein said liner has a soft upper surface.

9. The system as defined in claim 6 wherein said liner is made from a silicon elastomer.

10. The system as defined in claim 6 wherein said liner has a hinge line in its central portion.

11. The system as defined in claim 6 wherein a bottom of said platform portion has a feature to locate and secure said tray system to said support.

* * * * *